United States Patent [19]

Manyik et al.

[11] Patent Number: 4,899,003
[45] Date of Patent: Feb. 6, 1990

[54] PROCESS FOR OXYDEHYDROGENATION OF ETHANE TO ETHYLENE

[75] Inventors: Robert M. Manyik, St. Albans; Jonathan L. Brockwell, South Charleston; John E. Kendall, Charleston, all of W. Va.

[73] Assignee: Union Carbide Chemicals and Plastics Company Inc., Danbury, Conn.

[21] Appl. No.: 753,975

[22] Filed: Jul. 11, 1985

[51] Int. Cl.[4] .............................................. C07C 5/333
[52] U.S. Cl. ..................................... 585/313; 585/658; 585/659; 585/662
[58] Field of Search ............... 585/658, 659, 662, 663, 585/312, 313

[56] References Cited

U.S. PATENT DOCUMENTS

| | | | |
|---|---|---|---|
| 3,306,201 | 3/1967 | Bowers et al. ....................... | 585/658 |
| 3,674,887 | 7/1972 | Clay ...................................... | 585/658 |
| 3,728,413 | 4/1973 | Woerner .............................. | 585/658 |
| 4,150,063 | 4/1979 | Besozzi et al. ...................... | 585/656 |
| 4,195,188 | 3/1980 | Slinkard et al. ..................... | 585/658 |
| 4,250,346 | 2/1981 | Young et al. ........................ | 585/658 |
| 4,524,236 | 6/1985 | McCain ............................... | 585/658 |
| 4,568,790 | 2/1986 | McLain ............................... | 585/658 |

OTHER PUBLICATIONS

E. M. Thorsteinson et al., "Journal of Catalysis" pp. 116–132 (1978).

*Primary Examiner*—Asok Pal
*Attorney, Agent, or Firm*—Norman L. Balmer

[57] ABSTRACT

A process for the oxydehydrogenation of ethane to ethylene in a reaction system of open series connected stages, includes changing the total water and acetic acid content in the output gaseous stream after at least one stage other than the last stage of the series.

20 Claims, 4 Drawing Sheets

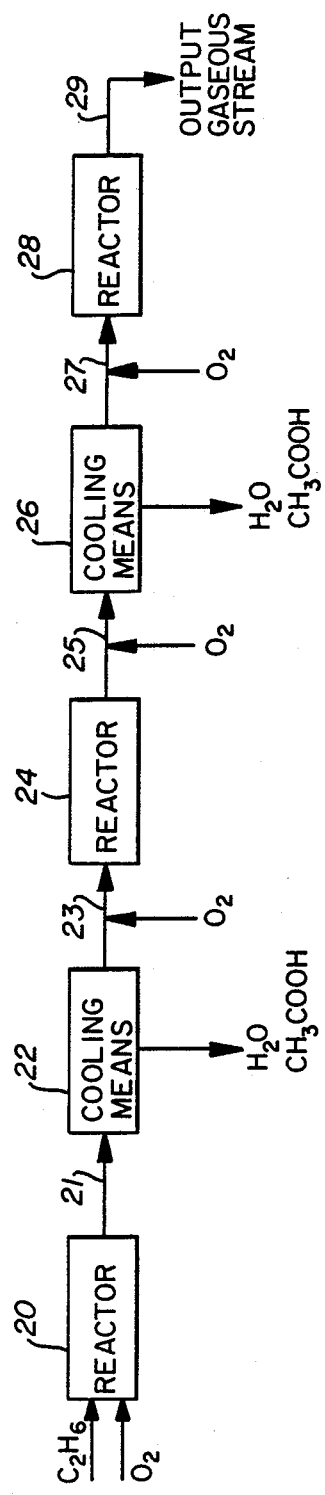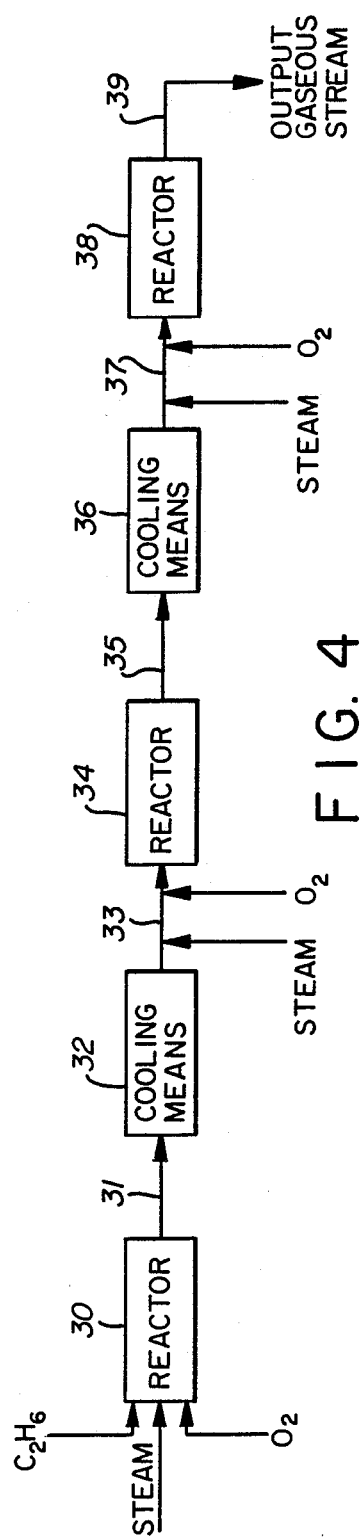

PROCESS FOR OXYDEHYDROGENATION OF ETHANE TO ETHYLENE

FIELD OF THE INVENTION

The invention relates to a process for the oxydehydrogenation of ethane to ethylene, and particularly to a process which uses a series arrangement of stages.

BACKGROUND OF THE INVENTION

The prior art discloses processes for the oxydehydrogenation of ethane to ethylene, but the processes disclosed use a single fixed bed of catalyst.

In particular, the prior art discloses the oxydehydrogenation of ethane to ethylene using low temperature catalysts which catalytically act on a mixture of ethane and oxygen to produce an output gaseous stream comprising ethylene, acetic acid, unreacted ethane, unreacted oxygen, and other gases such as CO and $CO_2$. Such catalysts and processes are disclosed in the article entitled, "The Oxidative Dehydrogenation of Ethane Over Catalysts Containing Mixed Oxides of Molybdenum and Vanadium" by E. M. Thorsteinson, T. P. Wilson, F. G. Young, and P. H. Kasai, in *Journal of Catalysis*, 52, p.p. 116–132 (1978). In addition, U.S. Pat. No. 4,250,346 discloses processes for low temperature catalytic oxydehydrogenation of ethane to ethylene and discloses many suitable catalysts.

SUMMARY OF THE INVENTION

The present invention relates to a process for converting ethane to ethylene, in a reaction system comprising at least two stages connected in open continuous series relationship with each other; each stage comprising an oxydehydrogenating catalyst system maintained at conditions for catalytically converting an input gaseous stream comprising ethane and oxygen to an output gaseous stream having a temperature greater than 250° C. and comprising ethylene, acetic acid, water, ethane, and oxygen; and the process comprising cooling the output gaseous stream of each stage other than the output gaseous stream of the last stage to a temperature less than about 250° C. for the introduction of oxygen; changing the total water and acetic acid content in the input gaseous stream of at least one stage with respect to the total water and acetic acid content in the output gaseous stream immediately preceding that stage; and supplying oxygen to the input gaseous stream of each stage when the input gaseous stream is at a temperature less than about 250° C. and in an amount such that the total oxygen content of the input gaseous stream of each stage is less than about 6 mole percent with respect to the total input gaseous stream of that stage.

In one preferred embodiment, a portion of both water and acetic acid are removed from the output gaseous stream of at least one stage other than the last stage of the series. In another preferred embodiment, water in the form of steam is added to the input gaseous stream of at least one stage other than the first stage of the series.

BRIEF DESCRIPTION OF THE DRAWINGS

FIG. 3 shows a block diagram of a portion of a system which uses one embodiment of the invention;

FIG. 4 shows a block diagram of a portion of a system which uses another embodiment of the invention;

DISCUSSION OF THE INVENTION

The invention enables the economical commercial production of ethylene and/or acetic acid. The process according to the invention utilizes a prior art catalyst system such that an input gaseous stream comprising ethane and oxygen under reaction conditions results in an output gaseous stream comprising ethylene, acetic acid, ethane, oxygen, as well as other gases. For such catalysts or catalyst systems, some of the stoichiometric equations for the reactions are as follows:

$$C_2H_6 + \tfrac{1}{2} O_2 \rightarrow C_2H_4 + H_2O$$
$$C_2H_6 + 3/2\, O_2 \rightarrow CH_3COOH + H_2O$$
$$C_2H_6 + (3/2 + x)O_2 \rightarrow 2CO_x + 3H_2O$$

x = 1 or 2

The ideal gas heats of reactions (600° K.) indicate the highly exothermic character of the process:

$$\Delta H_{C_2H_4} = -24.59 \text{ kcal/g-mole } C_2H_4$$
$$\Delta H_{CH_3COOH} = -116.54 \text{ kcal/g-mole } CH_3COOH$$
$$\Delta H_{CO} = -90.13 \text{ kcal/g-mole } CO$$
$$\Delta H_{CO_2} = -157.92 \text{ kcal/g-mole } CO_2$$

The measure of the usefulness of a catalyst is conveniently characterized by selectivity (ethane efficiency) to ethylene plus acetic acid, and conversion of ethane. The first term provides the mole percent of ethylene plus acetic acid produced with respect to the input stream of ethane while the second term provides the mole percent of carbon containing products produced by the catalyst (excluding the ethane in the output gaseous stream) with respect to the ethane in input gaseous stream. In carrying out the laboratory measurements, measurements were made in the examples for the mole content of ethane, ethylene, acetic acid, CO, and $CO_2$ in the output gaseous stream. These five components constitute the primary carbon containing products.

Based on this, the following equations have been used for calculations in the examples:

Selectivity (ethane efficiency) to ethylene plus acetic acid =

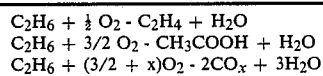

Conversion of ethane =

100 ×

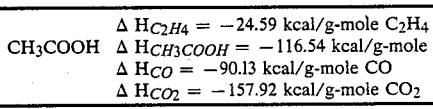

[ ] = moles

[$C_2H_6$] = moles of unconverted ethane

Figure 1:
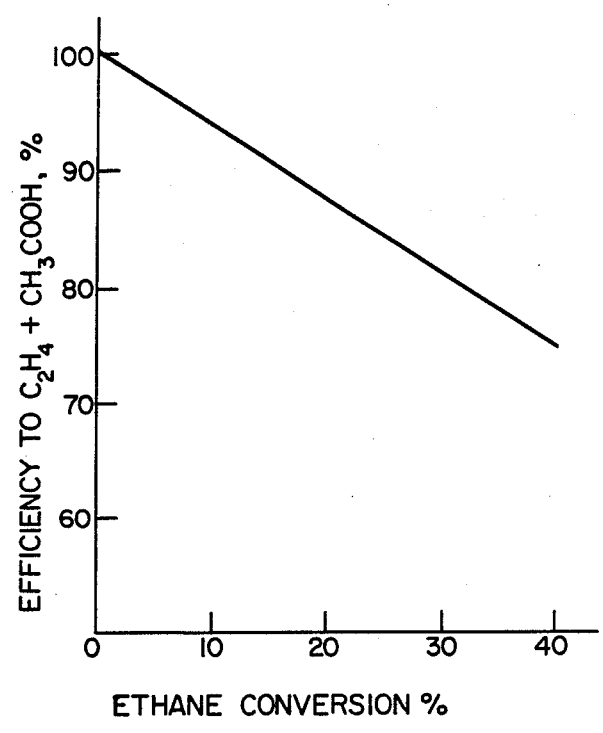
FIG. 1 shows a typical graph of selectivity to both ethylene plus acetic acid versus conversion of ethane for oxydehydrogenation of ethane.

Generally, the selectivity to ethylene plus acetic acid is approximately linearly related to the conversion of ethane over the preferred operating range. FIG. 1 shows a typical curve relating selectivity to ethylene plus acetic acid to conversion of ethane for a single stage containing a single fixed bed of catalyst. From this curve, it can be seen that selectivity to ethylene plus acetic acid declines with increasing ethane conversion from about 100 percent for about zero conversion of ethane.

The mole ratio of ethylene to acetic acid defines the relative yield of these products. It will be described herein, process steps for changing this ratio for use in a commercial viable process according to the invention. Thus, a commercial process can be carried out to favor the production of ethylene at the expense of acetic acid or to favor the production of acetic acid at the expense of ethylene.

Figure 2A:
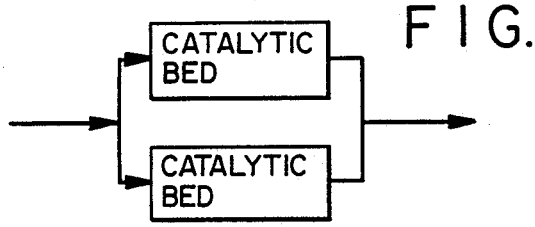
FIGS. 2A and 2B show parallel and series arrangements of stages or catalytic beds.
Figure 2B:
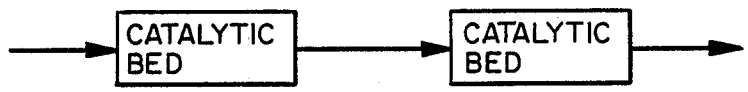

It has now been determined that a commercial viable process for the oxydehydrogenation of ethane to ethylene would require more than one catalytic bed to achieve economical operations. In this connection, some definitions used in the art will be considered. It can be seen that combination of stages or catalytic beds can be generally a parallel arrangement or a series arrangement as shown in FIGS. 2A and 2B, respectively.

A parallel arrangement as used herein described an arrangement of stages or catalytic beds in which the input gaseous stream of each stage or catalytic bed is a portion of a common input gaseous stream.

As used herein, a series arrangement of stages or catalytic beds is an arrangement of stages or catalytic beds in which a portion of the output gaseous stream of the first stage or catalytic bed forms a part of the input gaseous stream of the second stage or catalytic bed and each successive stage or catalytic bed is interconnected with the preceding stage or catalytic bed similarly; however, the portion of the output gaseous stream forming a part of the input gaseous stream of the successive stages or catalytic beds need not be identical.

The following is some background information with respect to a commercial process in general and particularly some of the parameters which urge certain process steps according to the invention.

From an analysis of processes for converting ethane to ethylene and acetic acid by catalytic oxydehydrogenation, it has been determined that a system preferably should have a conversion of ethane from about 10 percent to about 50 percent and more preferably about 20 percent to about 30 percent.

In order to operate such a process, consideration must be given to certain safety factors. It is known that the amount of oxygen in a gaseous stream containing hydrocarbons and at an elevated temperature must be limited in order to avoid ignition. The "limiting oxygen value" is defined herein as the oxygen mole concentration in a gaseous mixture for which there is a 50 percent probability of having combustion or burning reaction in the gaseous mixture under specific test conditions after exposing the gas mixture to a positive ignition source.

It has been determined from experiments designed to correlate to the instant process that the oxygen content in an input gaseous stream containing ethane should be less than about 6 mole percent of the input gaseous stream.

The temperature at which oxygen is introduced into the gaseous stream containing hydrocarbons must be less than the temperature for which autoignition can occur.

The "autoignition temperature" of a gas mixture, as defined herein, is the temperature at which the gas will ignite and sustain the combustion in the absence of an external ignition source. Autoignition is a complex thermal phenomenon which depends both on the properties of the gas mixture and on the characteristics of the system to which the gas is exposed. Autoignition can occur at the temperature for which there is a thermal instability in the balance between heat generated in the system by chemical reactions and the heat transferred across the system boundaries. Thus, the autoignition temperature is dependent on the system and is not an inherent property of the gas stream.

It has been determined from studies that there are two necessary and sufficient conditions for the autoignition temperature. One condition is that the rate of heat generated by the reaction equals the rate of heat transferred. The other is that the change in the rate of heat generated by the reaction with respect to the change in the operating temperature of the reaction is equal to the change in the rate of heat transfer with respect to a change in the temperature. These conditions constitute an instability because any increase in the temperature in the reaction will result in a corresponding increase in the temperature of the gases so that the gas temperatures can increase exponentially. This implies a potential runaway reaction and potentially explosive situation.

As a result of experimentations and evaluations, it was determined that oxygen introduced into a gaseous stream containing ethane and possibly ethylene should be carried out when the temperature of the gaseous stream is less than about 250° C.

A single stage having a conversion of ethane of greater than about 10 percent would be considered unsafe due to the required mole concentration of oxygen. Furthermore, a parallel arrangement of stages cannot provide a conversion of ethane in this range because the conversion of ethane is not additive for a parallel arrangement.

A series arrangement of stages does, however, provide a cumulative increase in the conversion of ethane. The unreacted ethane from any stage can be further converted in subsequent stages. The oxygen for the conversion can be supplied to each stage. Thus, the series arrangement of stages enables the safe achievement of the conversion of ethane for all levels.

Broadly, if each stage provided a conversion of ethane of about 8 percent or more, then three stages would provide a conversion of ethane of about 24 percent. There are, however, a number of factors which must be considered with respect to a series arrangement of stages. Some of the important factors will be considered herein.

It is preferable to operate each stage so that all of the oxygen in the input gaseous stream is not consumed because if all of the oxygen is consumed in a stage, the ethane can act as a reducing agent to the catalyst in that stage, thereby irreversibly damaging the catalyst. Preferably, the output gaseous stream of any stage contains about 0.2 mole percent of oxygen.

Except for the first stage, the input gaseous stream of each stage comprises ethane, ethylene, acetic acid, CO, $CO_2$, water, and gases which might be found in commercially available ethane. The effect of such an input gaseous stream on the performance and lifetime of a catalyst bed suitable for carrying out the invention must be considered in order to provide a commercial process which is economically advantageous. Commercial ethane typically contains methane, propane, and trace quantities of hydrogen sulfide, $CO_2$, and nitrogen. The methane has been found to be essentially unreactive in the presence of ethane, but propane has been found to be more reactive than ethane with most of it going to CO and $CO_2$ along with some amounts of propylene, acetic acid and other oxygenates.

Propane consumes oxygen to a greater extent than a similar amount of moles of ethane. Thus, the amount of propane in the feed must be considered with respect to the amount of oxygen required as well as the heat release and gas processing out of the last stage. Any hydrogen sulfide present does not poison the catalyst but oxidizes over the catalyst and contaminates the condensate in the gas processing after the last stage.

Experiments and analyses were carried out to establish rate models for the reactions which occur for the instant process.

The following important conclusions were determined as a result of extensive work:
(1) Ethylene inhibits ethylene formation.
(2) Ethane promotes ethylene formation.
(3) Temperature is a significant factor in each of the rates, an increase in temperature increases the rate of production of ethylene to a greater extent than the increase in the rate of production of acetic acid.
(4) Both ethane and ethylene propel the formation of CO and $CO_2$.
(5) Oxygen is significant in all of the rates.
(6) Water promotes the formation of acetic acid and inhibits the formation of ethylene.
(7) Ethane and ethylene have a significant impact on the rate at which acetic acid is formed.
(8) Catalyst age has a significant effect on each of the rates; the rates decline with increasing catalyst age.

The experimentation and analysis established that the output gaseous stream from one stage can be used to form part of the input gaseous stream of another stage. Of course, oxygen must be added as part of the input gaseous stream for a stage subsequent to the first stage.

The catalyst bed operates at a temperature greater than about 250° C. so that the output gaseous stream is at a temperature greater than about 250° C. Accordingly, it is essential to cool the output gaseous stream to a temperature below 250° C. before introducing oxygen to form the input gaseous stream of the subsequent stage in the series connected stages.

Pure oxygen or air can be used for the process. Oxygen can be supplied from an air separation unit. The use of air results in the necessity of separating nitrogen from the output gaseous stream of the last stage during the recovery of the ethylene. Such a separation requires additional costs over the cost of an air separation unit.

The interstage cooling of the gaseous stream provides an opportunity to carry out one of several critical process steps according to the invention. Water in the form of steam can be introduced into the interstage system to increase the amount of water in the input gaseous stream. The addition of water into the input gaseous stream increases the amount of oxygen which can be safely added to the input gaseous stream because the safe limit of the oxygen is relative to the entire mole content of the input gaseous stream. Furthermore, the addition of water increases the yield of acetic acid with respect to ethylene because water promotes the rate of formation of acetic acid while inhibiting the rate of formation of ethylene.

The water in the form of steam is preferably introduced into the output gaseous stream of a stage prior to introducing oxygen to form part of the input gaseous stream of a subsequent stage. Generally, the amount of water introduced is between about zero mole percent to about 10 mole percent and preferably from about 2 mole percent to about 6 mole percent of the input gaseous stream.

Another broad embodiment of the invention features the removal of water and acetic acid from the output gaseous stream between stages. Although it is only the water which need be removed, invariably acetic acid is removed. The removal of water is accomplished by cooling the output gaseous stream until the water condenses. When the water condenses, the acetic acid will also condense because of the acetic acid has a higher boiling point than water.

The removal of the water tends to change the distribution of the production of products in favor of ethylene at the expense of the acetic acid. That is, reducing the amount of water in the input gaseous stream results in the ratio of ethylene to acetic acid increasing with respect to the situation in which the water in the input gaseous stream is not reduced.

The implementation of the equipment to carry out the cooling of the output gaseous stream is straightforward technology. The use of a heat exchanger is common in the prior art for cooling a gaseous stream. Some consideration should be given to the extreme corrosive property of aqueous acetic acid at elevated temperatures. For this reason, it would be desirable to use pipes made of a material such as titanium in the equipment for which the condensation of the acetic acid will take place. Another suitable material is sold under the trademark of HASTELLOY C. Portions of the piping for which only cooling of the gaseous streams occurs can be made out of stainless steel.

The catalyst used in carrying out the instant process takes an input gaseous stream comprising ethane and oxygen and produces an output gaseous stream comprising ethylene, water, acetic acid, CO, $CO_2$, ethane, and oxygen. The ethane and oxygen are generally unreacted gases from the input gaseous stream. For the stages contemplated in carrying out the invention, the amount of unreacted oxygen in the output gaseous stream is about 0.2 mole percent.

Preferably, the process is operated at the pressures from about 1 to about 40 atmospheres, and more preferably from about 10 to about 25 atmospheres.

Preferably, the gas hourly space velocity (GHSV) per stage is from about 500 to about 6000 $h^{-1}$, and more preferably from about 2000 to about 5000 $h^{-1}$.

Some references have already been cited herein for disclosures on suitable catalysts. In addition, co-pending U.S. patent application Ser. No. 625,777, filed Jun. 28, 1984 now U.S. Pat. No. 4,524,236 discloses a process for oxydehydrogenating ethane to ethylene in a single stage and includes a description of a class of catalysts suitable for the instant invention and, moreover, the catalysts described in that patent application are the catalysts preferable for carrying out the instant invention.

The patent application discloses a calcined catalyst having the following composition:

$$Mo_aV_bNb_cSb_dX_e$$

X = at least one of the following: Li, Sc, Na, Be, Mg, Ca, Sr, Ba, Ti, Zr, Hf, Y, Ta, Cr, Fe, Co, Ni, Ce, La, Zn, Cd, Hg, Al, Ti, Pb, As, Bi, Te, U, Mn, and W; and a = 0.05 to 0.9
b = 0.1 to 0.4
c = 0.001 to 0.2
d = 0.001 to 0.1
e = 0.001 to 1.0

The values of a, b, c, d, and e constitute relative gram-atoms of the elements Mo, V, Nb, Sb, and X, respectively. The elements are present in combination with oxygen in the form of various oxides.

Generally, a solution is prepared of compounds of the metals selected for the catalyst, and either a particulate catalyst is formed or a supported catalyst is formed. The most preferred catalyst has the following formulation:

$$Mo_{16}V_{6.8}Nb_{1.9}Sb_{1.0}Ca_{1.0}$$

The following is a description of the preparation of the catalysts preferably for use in carrying out the instant invention.

A precursor solution of the compounds of the metals selected is prepared.

Preferably, the molybdenum is introduced into the solution in the form of ammonium salts such as ammonium paramolybdate, or organic acid salts of molybdenum such as acetates, oxalates, mandelates, and glycolates. Other partially water soluble molybdenum compounds which may be used include molybdenum oxides, molybdic acid, and chlorides of molybdenum.

Preferably, the vanadium is introduced into this solution in the form of ammonium salts such as ammonium meta-vanadate and ammonium decavanadate, or organic acid salts of vanadium such as acetates, oxalates and tartrates. Partially water soluble vanadium compounds such as vanadium oxides, and sulfates of vanadium can be used.

Preferably, the niobium and tantalum, when used are in the form of oxalates. Other sources of these metals in soluble form include compounds in which the metal is coordinated, bonded or complexed to a beta-diketonate, carboxylic acid, an amine, an alcohol, or/and alkanolamine.

Preferably, the antimony is introduced into solution in the form of antimony oxalate. Other soluble and insoluble compounds of antimony can be used such as antimony oxide and antimony chloride.

The X component of the catalyst can be soluble or insoluble compounds, preferably soluble. Compounds which are strongly reducing may adversely affect the oxidation states of the metals.

The following are some preferable compounds for the X components. One is titanium in the form of a water soluble chelate coordinated with ammonium lactate, and others are titanium compounds in which the metal is coordinated, or complexed in a beta-diketonate, a carboxylic acid, an amine, an alcohol and/or alkanolamine. Generally, nitrates are desirable along with water soluble chlorides and organic acid salts such as acetates, oxalates, tartrates, lactates, salicylates, formates, and carbonates. Preferred compounds for tungsten are in the form of ammonium salts such as ammonium paratungstate or other water soluble compounds such as tungstic acids.

The precursor solution is dried rapidly and the solids are heated in air for about 5 hours at a temperature of about 350° C. to activate the catalyst.

Preferably, a supported catalyst is used. It is prepared by the following general procedure. The vanadium compound is mixed with water to form a first mixture; the niobium compound and antimony compound are mixed with water to form a second mixture; and the molybdenum compound is mixed with water to form a third mixture. Any X compounds which are ammonium salts are mixed with the first mixture. Otherwise, X compounds are mixed into the second mixture. The first and second mixtures are heated and mixed separately for about fifteen minutes; and then combined and mixed with heating for about fifteen minutes. The third mixture is heated and mixed, and then added to the combined first and second mixtures to form a precursor mixture. After mixing and heating of the precursor mixture for about fifteen minutes, the precursor mixture is ready for the next step, separation of the water soluble portion of the mixture.

The separation can be carried out simply by decanting the soluble portion or by filtering. The filtering can be carried out using sintered glass, or a paper filter with or without suction. The soluble portion is used to impregnate the support. The support is dried rapidly in air usually, but the drying can be carried out in an inert atmosphere.

The suitable supports include silica, aluminum oxide, silicon carbide, zirconia, titania, and mixtures thereof.

Preferably, the support has relatively low surface area, less than about 1.0 square meter per gram, and relatively large pores, median pore diameter greater than about 10 microns. Table I shows a variety of commercially available supports suitable for carrying out the invention.

TABLE I

| SUPPORT | COMPOSITION (%) Al₂O₃ | SiO₂ | Others | SIZE (IN) | SHAPE | SURFACE AREA M²/g | PORE VOLUME CC | APPARENT DENSITY g/CC | PORE SIZE DISTRIBUTION 10% MICRONS | 50% MICRONS | 90% MICRONS | APPARENT POROSITY % | LEACHABLE (a) ppm Na | K | Ca | Mg |
|---|---|---|---|---|---|---|---|---|---|---|---|---|---|---|---|---|
| 1 | 89.4 | 9.3 | | ⅛ | PELLETS | .81–.87 | .21–.29 | | 120.00 | 29.0 | 9.0 | 45–50 | | | | |
| 2 | 99.6 | | | 3/16 | PELLETS | .7–1.3 | .25–.34 | | 190.00 | 1.2 | 8.5 | 50–56 | | | | |
| 3 | 99.6 | | | ¼ | RINGS | .7–1.3 | .25–.34 | | 3.00 | 1.2 | 8.5 | 50–56 | | | | |
| 4 | 86.9 | 11.6 | | ¼ | PELLETS | .02–.08 | .17–.25 | | | 18.0 | 6.0 | 39–45 | | | | |
| 5 | 86.1 | 11.8 | | ¼ | SPHERES | .0095 | .18–.26 | | 350.00 | 130.0 | 45.0 | 49–55 | 7.8 | | 2.0 | |
| 6 | 86.1 | 11.8 | | ¼ | SPHERES | .005–.95 | .18–.26 | | | 130.0 | 45.0 | 49–55 | | | | 4 |
| 7 | 87.0 | 11.4 | | ⅛ | PELLETS | .0450 | .28 | 3.22 | 73.00 | 26.0 | 8.0 | 47–54 | 9.0 | 2 | 0.5 | 2 |
| 8 | 87.0 | 11.4 | | ⅛ | PELLETS | .0640 | 0.290 | 3.00 | 157.00 | 29.0 | 9.0 | 50.7 | 9.0 | 3 | 2.0 | 1 |
| 9 | 85.5 | 12.6 | | 3/16 | SPHERES | .0640 | .21–.27 | 3.85 | 65.00 | 35.0 | 9.0 | 46–52 | | | | |
| 10 | 86.1 | 12.0 | | ¼ | SPHERES | .005–.04 | .15–.25 | | 190.00 | 75.0 | 35.0 | 37–42 | | | | |
| 11 | | | (b) | 5/16 | RINGS | .34 | .550 | 2.6 | 90.0 | 23.0 | 2.0 | | | | | |
| 12 | 86.2 | 12.4 | | 5/16 | RINGS | 0.1720 | 0.464 | | 130.00 | 21.0 | 2.6 | 59.4 | 8.0 | 5 | 1.0 | 2 |
| 13 | ZrO₂ | CaO | | ¼ | SPHERES | 0.1020 | 0.155 | 3.15 | 295.00 | 32.0 | 6.0 | 43.9 | | | | |
| 14 | | 100.0 | | | POWDER | 3.0 | | | | 0.7 | | | | | | |
| 15 | | | (c) | 5/16 | RINGS | 0.0890 | 0.390 | | 86.0 | 22.0 | 7.0 | 58.3 | 0.8 | 2125 | 129 | 21 (d) |
| 16 | | 100.0 | | | POWDER | 1–3.5 | | | | 7.0 | | | | | | |

(a) Norton Co. C.P.T.D. Test Method No. 63–78, "Determination of Nitric Acid Soluble Na, K, Ca, and Mg In Alumina Catalyst Carriers."
(b) Alumina with clay binder
(c) Silica fused with glass, crushed to size
(d) Other leachables ppm: Al-182, Fe-40; P-56; Si-104; B-184; Mo-325.

It is known that the catalyst undergoes an aging process during its use and this results in a decline in the reaction rates. Catalyst regeneration can be carried out to maintain the performance of the catalyst. The catalyst can be regenerated by oxidation with dilute oxygen such as 5 volume percent oxygen and nitrogen in situ at a temperature of from about 350° C. to about 400° C. for from about one to about 24 hours, preferably about 10 hours.

FIG. 3 shows a block diagram of a portion of a process system incorporating one embodiment of the invention.

FIG. 3 shows a system comprising three reactors with interstage cooling to remove water and acetic acid. Ethane and oxygen comprise the input gaseous stream to reactor 20. As used herein, a reactor comprises at least one catalytic bed for the oxydehydrogenation of ethane to ethylene. A plurality of catalytic beds within a single reactor would be arranged preferably in parallel but could be in series or a combination thereof. The reactor 20 is preferably an arrangement of tubes each containing a catalyst bed with the tubes enclosed in a shell to provide temperature control. Such an arrangement in the art is referred to as a "shell and tube geometry". Typically, the tube can have an inside diameter of about 2.5 to about 4.0 centimeters and a length of from about 6 to about 12 meters. Each shell would contain as many tubes as needed for the desired production capacity. The tubes are in a parallel arrangement with each other. The use of separate tubes within the shell is advantageous for temperature control in the tubes. The input gaseous stream is divided into the tubes and a liquid such as the trademark DOWTHERM A sold by Dow Chemical Company circulates around the tubes and within the shell to maintain the operating temperature. The primary component of DOWTHERM A is diphenyl ether. Another suitable liquid for maintaining the temperature is a mixture of isomeric dibenzyl benzenes such as a product sold under the trademark MARLOTHERM S by Chemische Werke Huls AG. Other liquids which appear to be suitable based on their boiling temperatures at atmospheric pressure include tetracontane and pentatricontane. In addition, molten salts can be used.

Typically, the gas hourly space velocity (GHSV) for the reactor 20 is from about 2000 to about 5000 $h^{-1}$. The pressure is from about 10 to about 20 atmospheres with an input oxygen content of about 6 mole percent of the entire input gaseous stream. The output gaseous stream 21 contains unreacted ethane, unreacted oxygen, ethylene, acetic acid, and other gases such as gases which were present in the commercial ethane and gases produced by the reaction such as CO and $CO_2$. The output gaseous stream 21 communicates to cooling means 22 which simply cools the output gaseous stream 21 so that the water and acetic acid in output gaseous stream 21 condense. As pointed out, the condensate can be extremely corrosive so that the materials used should be selected to resist the corrosion. Portions of the equipment exposed to hot condensing acetic acid vapors can be fabricated from titanium or HASTELLOY C. Portions of the equipment in contact with cool solutions of acetic acid can be made out of stainless steel. Equipment which will be exposed to acetic acid vapors at high temperatures such as the reactor tubes can be fabricated from carbon steel.

The choice of materials used should be selected to avoid catalyst poisons. For example, metals such as iron and nickel can react with CO under certain conditions to produce volatile metal carbonyls. The metal carbonyls can be decomposed over the catalyst to deposit metal oxides on the catalyst surface and thereby alter the activity and performance of the catalyst.

The cooling means 22 can be a heat exchanger or any other well known prior art equipment for cooling the water and acetic acid so that they condense. The water and acetic acid are removed from cooling means 22 and the remaining gas is combined with oxygen to form the input gaseous stream 23 which enters reactor 24. Reactor 24 is essentially the same as reactor 20.

The reactor 24 produces an output gaseous stream 25 which enters cooling means 26 which is similar to cooling means 22. After the water and acetic acid have been removed the remaining gas in cooling means 26 is combined with oxygen to form input gaseous stream 27 into reactor 28. Reactor 28 is similar to reactor 23. The reactor 28 produces an output gaseous stream 29.

The output gaseous stream 29 includes ethylene, ethane, oxygen, acetic acid, water, and some other gases as indicated above.

For convenience, as used herein the term "stage" comprises a reactor for catalytically oxydehydrogenating ethane to ethylene. The "last stage" referred to herein is the "output stage" in accordance with common practice in the process art. Also, system components such as the cooling means 22 is interstage equipment in accordance with common practice in the process art.

Another important embodiment is shown in FIG. 4. Ethane, oxygen and water in the form of steam enter reactor 30 to produce an output gaseous stream 31 which enters cooling means 32. Cooling means 32 reduces the temperature of the output gaseous stream 21 to a temperature below about 250° C. including added oxygen and water in the form of steam enters reactor 34 to produce an output gaseous stream 35. The output gaseous stream 35 enters the cooling means 36 which is similar to cooling means 32. The output gaseous stream 35 is cooled to less than about 250° C. and oxygen and water in the form of steam are introduced to produce an input gaseous stream 37 which enters reactor 38 to produce an output gaseous stream 39.

Figure 5:
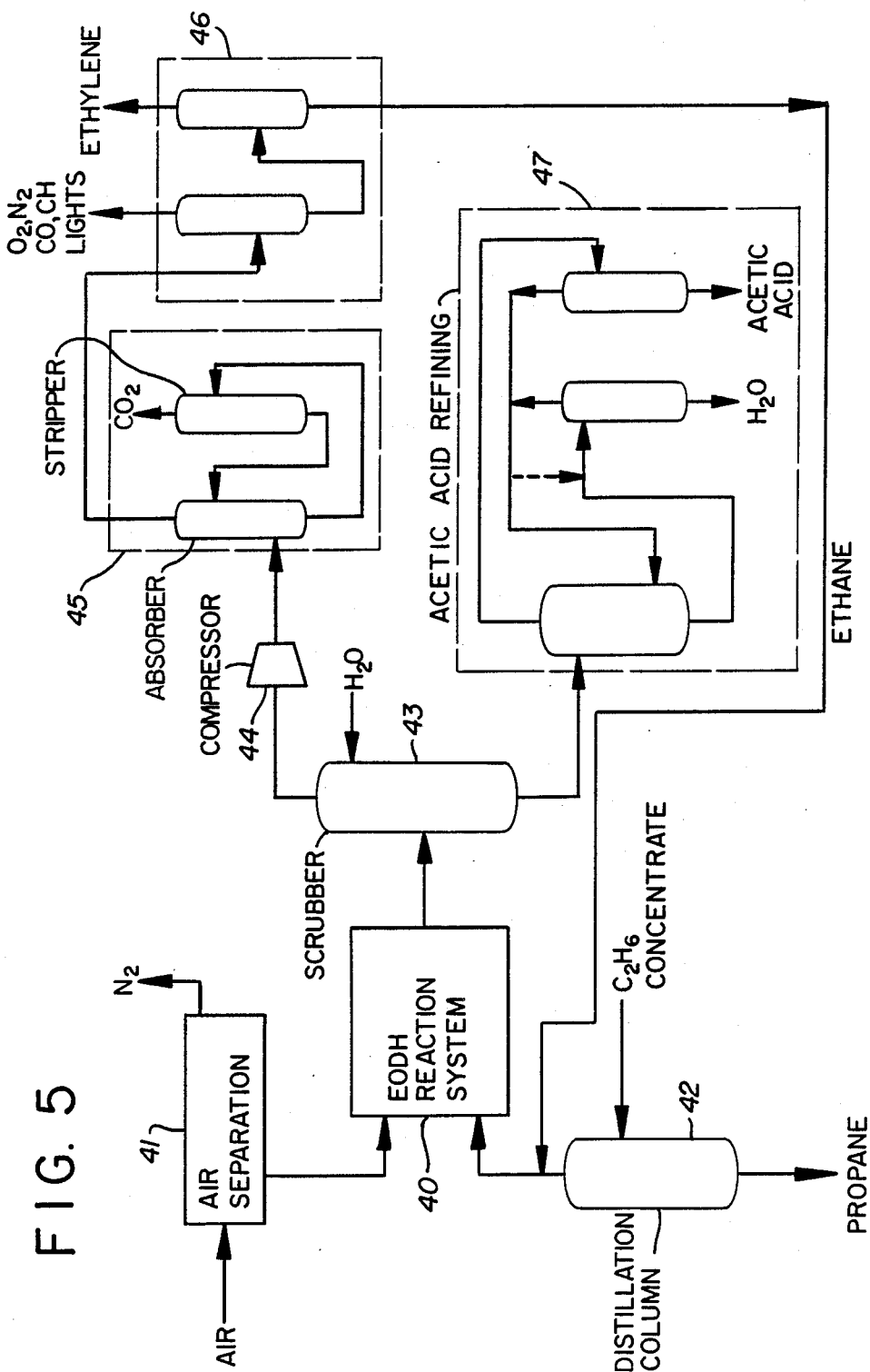
FIG. 5 shows a block diagram of a commercial system using the invention.

The systems shown in FIGS. 3 and 4 in relationship to an overall commercial system is shown in simplified form in FIG. 5. In FIG. 5, the EODH reaction system 40 corresponds to essentially all of the blocks shown in either FIG. 3 or FIG. 4. Oxygen is supplied to the EODH reaction system 40 from an air separation unit 41. The ethane into the EODH reaction system 40 comprises recycled ethane from unit 46 and ethane from the distillation column 42 which separates out propane which may be present in the commercial ethane. The output of the EODH reaction system 40 goes to a scrubber 43 which separates out the aqueous acetic acid. The gases from the scrubber 43 go to a compressor 44 and then to unit 45 which separates out $CO_2$. Unit 45 is a prior art unit which could comprise a portion which absorbs $CO_2$ with a solvent such as alkanolamine followed by a stripper which removes the absorbed $CO_2$. The gases then pass to unit 46 which contains distillation columns for separating out ethylene, ethane, and various "lights" such as $O_2$, $N_2$, CO and $CH_4$. The ethane from unit 46 is recycled to the EODH reaction system 40. The aqueous acetic acid from the scrubber 43 goes through an acetic acid refining unit 47 which separates out water and acetic acid.

A 2-stage pilot plant was built and operated. Each reaction stage is a tube having dimensions contemplated as being suitable for commercial operations. The capability to feed gases such as steam, acetic acid, ethylene, CO, and $CO_2$ together with ethane and oxygen enabled the simulation of any two series connected stages in a multistage open series arrangement.

Figure 6:
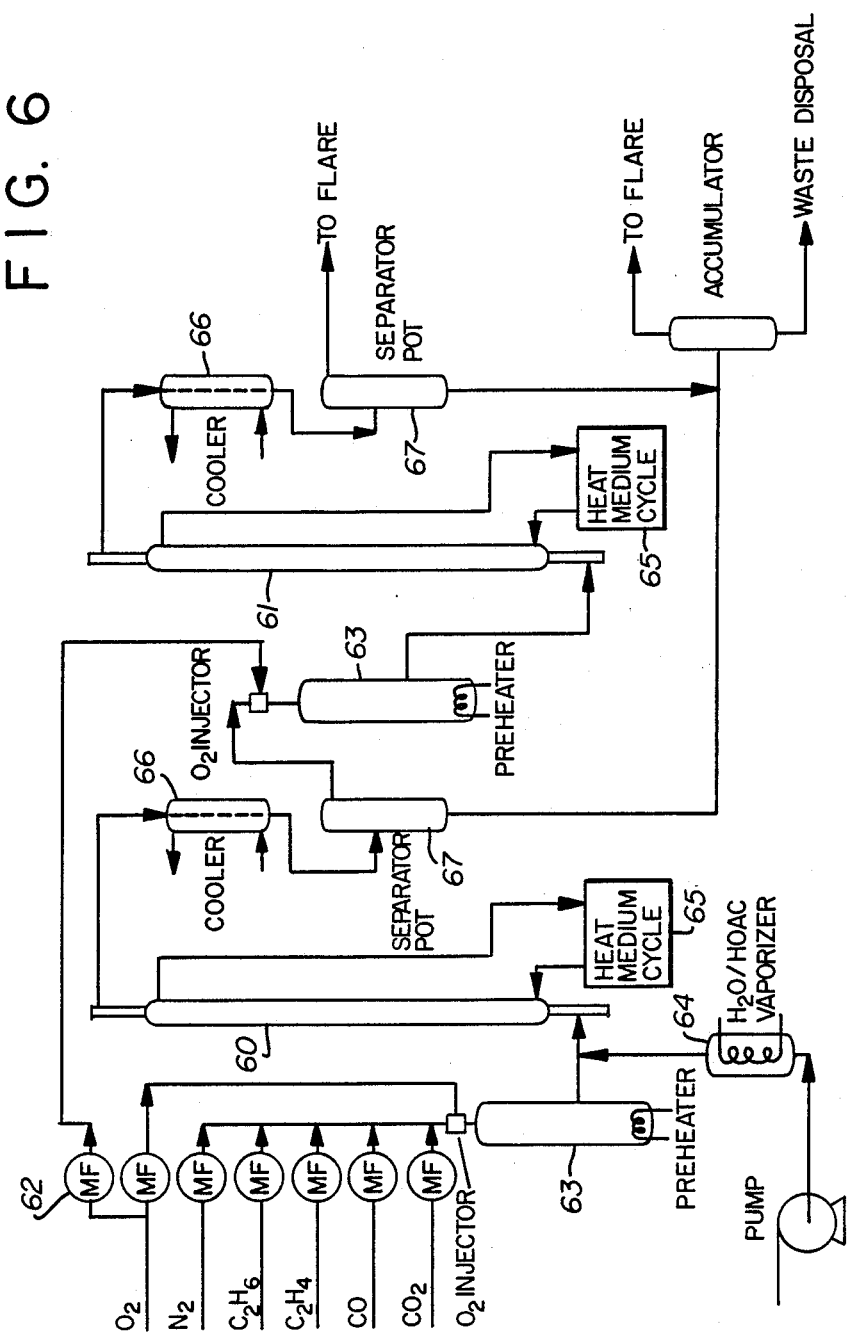
FIG. 6 shows a block diagram of a pilot plant system used to obtain data relating to the invention.

FIG. 6 shows a block diagram of the pilot plant used.

Each reactor 60 and 61 comprised a tube about 7.62 meters long having an inside diameter of about 2.6 cm. The bottom 1.8 meters of the tube was packed with glass beads having an average diameter of about 0.6 cm. The glass beads served as a secondary preheating section for raising the feed gases to the reaction temperature. The tube was packed with about 4.6 meters of a catalyst and the remaining portion of the tube was packed with glass beads of the type used in the bottom portion. The reaction temperature was controlled by circulating a heat transfer fluid through a jacket around the tube. The transfer fluid used was MARLOTHERM S. The catalyst used had the following gram-atom ratios:

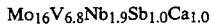

$Mo_{16}V_{6.8}Nb_{1.9}Sb_{1.0}Ca_{1.0}$

Support 12 of Table 1 was used. The gases $O_2$, $N_2$, $C_2H_6$, $C_2H_4$, CO, and $CO_2$ were supplied through respective mass flowmeters 62. These gases were preheated in heating unit 63 prior to being supplied to the reactor 60. Any water or aqueous acetic acid being supplied to a reactor 60 was vaporized in a heating unit 64. The hot heat transfer fluid was circulated through the reactors 60 and 61 with unit 65 which also controlled the temperature within a preset range.

The output gaseous stream from the reactors 60 and 61 were cooled in the respective cooling means 66. The respective output gaseous streams were then passed to a separator unit 67 which was used to separate and accumulate aqueous acetic acid from the gas stream. Oxygen was injected between the stages in accordance with the invention.

The input and output gaseous streams of the reactors 60 and 61 were analyzed using gas chromatographs.

The pilot plant shown in FIG. 6 had only two stages; however, the data were collected to simulate more than two stages and enabled a computer simulation of systems having more than two stages.

EXAMPLES

The Examples were carried out to compare operations with and without the invention.

EXAMPLE 1

A 2-stage series connected system was evaluated in the pilot plant for operation with and without interstage removal of water and acetic acid (aqueous acetic acid). For each case, about 6 mole percent of oxygen was used for each stage. Tables 2 and 3 correspond respectively to the operation of the 2-stage system with and without the interstage removal of water and acetic acid. For Table 2, the total output includes the gaseous output stream of stage 2 and also the $H_2O$ and $CH_3COOH$ removed before stage 2. The $CH_3COOH$ system selectivity is for the total $CH_3COOH$ from both the interstage removal and the output of stage 2.

TABLE 2

| INTERSTAGE REMOVAL OF WATER AND ACETIC ACID FOR 2-STAGES | | |
|---|---|---|
| | COMPOSITION IN MOLE PERCENT | |
| | INPUT STAGE 1 | TOTAL OUTPUT |
| $C_2H_6$ | 93.83 | 76.63 |
| $O_2$ | 5.93 | 1.44 |
| $CO_2$ | 0.25 | 0.59 |
| $C_2H_4$ | 0 | 7.66 |
| $CH_3COOH$ | 0 | 1.55 |
| $H_2O$ | 0 | 11.25 |
| CO | 0 | 0.88 |

About 98% of $H_2O$ removed interstage.
SYSTEM ETHANE CONVERSION = 11.4%
$C_2H_4$ SYSTEM SELECTIVITY = 78.0%
$CH_3COOH$ SYSTEM SELECTIVITY = 15.8%

TABLE 3

| NO INTERSTAGE REMOVAL OF WATER AND ACETIC ACID FOR 2-STAGES | | |
|---|---|---|
| | COMPOSITION IN MOLE PERCENT | |
| | INPUT STAGE 1 | OUTPUT STAGE 2 |
| $C_2H_6$ | 93.87 | 76.84 |
| $O_2$ | 5.88 | 1.28 |
| $CO_2$ | 0.25 | 0.67 |
| $C_2H_4$ | 0 | 7.37 |
| $CH_3COOH$ | 0 | 1.62 |
| $H_2O$ | 0 | 11.24 |
| CO | 0 | 0.98 |

SYSTEM ETHANE CONVERSION = 11.2%
$C_2H_4$ SYSTEM SELECTIVITY = 76.0%
$CH_3COOH$ SYSTEM SELECTIVITY = 16.6%

From Tables 2 and 3, it can be appreciated that the 2-stage system with interstage removal of water and acetic acid had a higher ethylene system selectivity and a lower acetic acid system selectivity as compared to the 2-stage system which did not have interstage removal of water and acetic acid.

EXAMPLE 2

In this Example, a 4-stage series connected system was simulated. The simulation was carried out with and without the removal of water and acetic acid in the interstages. For each run a fixed ethane input to the first stage was assumed and the oxygen input to each stage was taken as about 5 mole percent of the input gaseous stream of that stage. The temperature of the input gaseous stream of each stage was adjusted to produce an operating temperature for which the output gaseous stream included about 0.2 mole percent oxygen.

Removing water and acetic acid from the output gaseous stream of a stage reduces the flow rate of the input gaseous stream to the subsequent stages. This results in the subsequent stages having relatively lower operating temperatures as compared to a system without the removal of water. The lower temperatures would tend to reduce the rate of production of ethylene relative to the rate of production of acetic acid. Nevertheless, a higher system selectivity to ethylene is obtained for a process for which there is interstage removal of water.

For such a system, Table 4 shows the system output composition with and without the removal of water and acetic acid after each of the intermediate stages. For the interstage removal of water and acetic acid, Table 4 shows calculations based on total water and acetic acid out of all of the stages.

TABLE 4

4-STAGE SYSTEM WITH AND WITHOUT REMOVAL OF WATER AND ACETIC ACID

COMPOSITION IN MOLE PERCENT

| | TOTAL OUTPUT WITH REMOVAL | OUTPUT WITHOUT REMOVAL |
|---|---|---|
| $C_2H_6$ | 58.49 | 58.00 |
| $O_2$ | 0.17 | 0.16 |
| $CO_2$ | 1.06 | 1.27 |
| $C_2H_4$ | 13.60 | 12.11 |
| $CH_3COOH$ | 2.67 | 4.00 |
| $H_2O$ | 21.43 | 21.77 |
| CO | 2.58 | 2.69 |

SYSTEM ETHANE CONVERSION (WITH REMOVAL) = 23.3%
SYSTEM ETHANE CONVERSION (WITHOUT REMOVAL) = 23.5%
$C_2H_4$ SYSTEM SELECTIVITY (WITH REMOVAL) = 74.8%
$C_2H_4$ SYSTEM SELECTIVITY (WITHOUT REMOVAL) = 66.4%
$CH_3COOH$ SYSTEM SELECTIVITY (WITH REMOVAL) = 15.0%
$CH_3COOH$ SYSTEM SELECTIVITY (WITHOUT REMOVAL) = 22.5%

Table 5 shows the average temperature of each of the stages for the two runs.

TABLE 5

| | Stage 1 | Stage 2 | Stage 3 | Stage 4 |
|---|---|---|---|---|
| With Removal | 358.8° C. | 365.6° C. | 371.4° C. | 374.6° C. |
| Without Removal | 358.8° C. | 369.4° C. | 376.3° C. | 383.2° C. |

From Table 4, it can be seen that the interstage removal of water and acetic acid results in a higher ethylene system selectivity and a lower acetic acid system selectivity as compared to the system without interstage removal of water and acetic acid.

EXAMPLE 3

This Example is similar to Example 2 except that the 4-stage simulation was used to compare a system with and without the addition of water to each stage. It was assumed that 2½ mole percent of water was added to the input gaseous stream of the first stage and that each stage thereafter had an identical mass amount of water added to the respective input gaseous stream.

Adding water to a stage would require a higher operating temperature for the stage and this would tend to decrease the rate of production of acetic acid relative to the rate of production of ethylene. It is found, however, that the system in which water is added to the stages has a greater selectivity to acetic acid.

Table 6 summarizes the results of the two runs.

TABLE 6

4-STAGE SYSTEM WITH AND WITHOUT THE ADDITION OF WATER

COMPOSITION IN MOLE PERCENT

| | OUTPUT WITH ADDED WATER | OUTPUT WITHOUT ADDED WATER |
|---|---|---|
| $C_2H_6$ | 53.13 | 58.00 |
| $O_2$ | 0.22 | 0.16 |
| $CO_2$ | 1.32 | 1.27 |
| $C_2H_4$ | 10.54 | 12.11 |
| $CH_3COOH$ | 4.23 | 4.00 |
| $H_2O$ | 28.01 | 21.77 |
| CO | 2.55 | 2.69 |

SYSTEM ETHANE CONVERSION (WITH ADDED) = 23.6%
SYSTEM ETHANE CONVERSION (WITHOUT ADDED) = 23.5%
$C_2H_4$ SYSTEM SELECTIVITY (WITH ADDED) = 62.5%
$C_2H_4$ SYSTEM SELECTIVITY (WITHOUT ADDED) = 66.4%
$CH_3COOH$ SYSTEM SELECTIVITY (WITH ADDED) = 25.7%
$CH_3COOH$ SYSTEM SELECTIVITY (WITHOUT ADDED) = 22.5%

Table 7 shows the average temperature of each of the stages for the two runs.

TABLE 7

| | Stage 1 | Stage 2 | Stage 3 | Stage 4 |
|---|---|---|---|---|
| With Added | 360.3° C. | 372.7° C. | 379.7° C. | 386.8° C. |
| Without Added | 358.8° C. | 369.4° C. | 376.3° C. | 383.2° C. |

From Table 6, it can be seen that the addition of water to the input gaseous stream of each stage results in a higher acetic acid system selectivity and a lower ethylene system selectivity compared to the system without any interstage addition of water.

We claim:

1. A process for converting ethane to ethylene, in a reaction system comprising:
   at least two stages connected in open continuous series relationship with each other;
   each stage comprising an oxydehydrogenating catalyst system maintained at conditions for catalytically converting an input gaseous stream comprising ethane and oxygen to an output gaseous stream having a temperature greater than 250° C. and comprising ethylene, acetic acid, water, ethane, and oxygen;
   comprising the steps of:
   cooling the output gaseous stream of each stage other than the output gaseous stream of the last stage to a temperature of less than about 250° C. for the introduction of oxygen;
   changing the total water and acetic acid content in the input gaseous stream of at least one stage with respect to the total water and acetic acid content in the output gaseous stream immediately preceding that stage; and
   supplying oxygen to the input gaseous stream of each stage when the input gaseous stream is at a temperature of less than about 250° C. and in an amount such that the total oxygen content of the input gaseous stream of each stage is less than about 6 mole percent with respect to the total input gaseous stream of that stage.

2. The process of claim 1, wherein at least a portion of the water and acetic acid are removed from the output gaseous stream of at least one stage other than the last stage of the series.

3. The process of claim 1, wherein water in the form of steam is added to the input gaseous stream of at least one stage.

4. The process of claim 1, wherein there are three stages in series connection with each other.

5. The process of claim 1, wherein there are four stages in series connection with each other.

6. The process of claim 1, wherein there are at least three intermediate stages, and water and acetic acid are removed from the output gaseous stream of each of the stages other than the last stage of the series.

7. The process of claim 1, wherein the gases through each stage has a gas hourly space velocity of from about 500 to about 6000 $h^{-1}$.

8. The process of claim 7, wherein the gases through each stage has a gas hourly space velocity of from about 2000 to about 5000 $h^{-1}$.

9. The process of claim 1, wherein each stage is at a pressure of from about 1 to about 40 atmospheres.

10. The process of claim 9, wherein each stage is at a pressure of from about 10 to about 25 atmospheres.

11. The process of claim 1, wherein each catalyst system comprises a supported catalyst.

12. The process of claim 11, wherein said support has a surface area less than about 1.0 $m^2/g$ and a median pore diameter greater than about 10 microns.

13. The process of claim 1, wherein the output gaseous stream of each stage comprises oxygen.

14. The process of claim 13, wherein the output gaseous stream of each stage comprises about 0.2 mole percent oxygen.

15. The process of claim 14, wherein the input gaseous stream of each stage comprises about 5 mole percent oxygen.

16. The process of claim 1, wherein the overall conversion of ethane of all the stages is from about 10 percent to about 50 percent.

17. The process of claim 16, wherein the overall conversion of ethane of all the stages is from about 20 percent to about 30 percent.

18. The process of claim 1, further comprising separating most of the ethylene from the output gaseous stream of the last stage of the series.

19. The process of claim 1, further comprising separating most of the ethane from the output gaseous stream of the output stage and using at least a portion of the separated ethane as part of the input gaseous stream of the first stage of the series.

20. The process of claim 1, further comprising separating the acetic acid from the output gaseous stream of the last stage of the series.

* * * * *

UNITED STATES PATENT AND TRADEMARK OFFICE
CERTIFICATE OF CORRECTION

PATENT NO. : 4,899,003

DATED : February 6, 1990

INVENTOR(S) : Robert M. Manyik, et al.

It is certified that error appears in the above-identified patent and that said Letters Patent is hereby corrected as shown below:

Column 12, line 36, before "including" insert --so that oxygen of less than about 6 mole percent can be introduced safely. The input gaseous stream 33--.

Signed and Sealed this

Fifth Day of March, 1991

Attest:

HARRY F. MANBECK, JR.

*Attesting Officer*     *Commissioner of Patents and Trademarks*